(12) United States Patent
Schwartz

(10) Patent No.: US 11,786,140 B2
(45) Date of Patent: Oct. 17, 2023

(54) CONTROLLED-FLOW INFUSION CATHETER AND METHOD

(71) Applicant: CorFlow Therapeutics AG, Baar (CH)

(72) Inventor: Robert S. Schwartz, Inver Grove Heights, MN (US)

(73) Assignee: CorFlow Therapeutics AG, Baar (CH)

( * ) Notice: Subject to any disclaimer, the term of this patent is extended or adjusted under 35 U.S.C. 154(b) by 505 days.

(21) Appl. No.: 17/000,240

(22) Filed: Aug. 21, 2020

(65) Prior Publication Data

US 2021/0052168 A1  Feb. 25, 2021

Related U.S. Application Data

(60) Provisional application No. 62/889,984, filed on Aug. 21, 2019.

(51) Int. Cl.
*A61B 5/026* (2006.01)
*A61B 5/00* (2006.01)
*A61M 5/142* (2006.01)

(52) U.S. Cl.
CPC ............ *A61B 5/026* (2013.01); *A61B 5/6851* (2013.01); *A61B 5/6853* (2013.01); *A61B 2562/0247* (2013.01); *A61M 5/142* (2013.01)

(58) Field of Classification Search
CPC ................ A61B 5/026; A61B 5/02158; A61B 5/6851–6853; A61B 2562/0247
See application file for complete search history.

(56) References Cited

U.S. PATENT DOCUMENTS

| | | |
|---|---|---|
| 4,689,041 A | 8/1987 | Corday et al. |
| 6,156,005 A | 12/2000 | Theron |
| 6,295,990 B1 | 10/2001 | Lewis et al. |
| 6,423,032 B2 | 7/2002 | Parodi |
| 6,485,500 B1 | 11/2002 | Kokish et al. |
| 6,488,671 B1 | 12/2002 | Constantz et al. |
| 7,722,596 B2 | 5/2010 | Shapland et al. |
| 7,837,650 B1 | 11/2010 | Cox et al. |
| 8,177,704 B1 | 5/2012 | Mohl et al. |
| 8,366,659 B2 | 2/2013 | Ehrenreich et al. |
| 8,430,861 B2 | 4/2013 | Schwartz et al. |

(Continued)

FOREIGN PATENT DOCUMENTS

| | | |
|---|---|---|
| AU | 2017205404 A1 | 7/2018 |
| CA | 3010447 A1 | 7/2017 |

(Continued)

OTHER PUBLICATIONS

Costa, et al., "Mimicking Arterial Thrombosis in a 3d-printed Microfluidic in Vitro Vascular Model Based on Computed Tomography Angiography Data," Lab on a Chip, Royal Society of Chemistry, 17(16):2785-2792 (Jun. 2017).

(Continued)

*Primary Examiner* — Kaylee R Wilson
*Assistant Examiner* — Raymond P Dulman
(74) *Attorney, Agent, or Firm* — Eversheds Sutherland (US) LLP; Christopher C. Bolten; Regis C. Worley, Jr.

(57) ABSTRACT

Devices and methods for determining fluid flow resistance at a targeted location in a bodily fluid vessel by monitoring changes in pressure gradients across the location while fluid flow is being manipulated by introducing infusate into the target area at different rates.

20 Claims, 8 Drawing Sheets

(56) References Cited

U.S. PATENT DOCUMENTS

| | | | |
|---|---|---|---|
| 8,540,669 B2 | 9/2013 | Ehrenreich et al. | |
| 8,708,996 B2 | 4/2014 | Consigny et al. | |
| 8,876,850 B1 | 11/2014 | Vollmers et al. | |
| 9,174,020 B2 | 11/2015 | Allen et al. | |
| 9,205,226 B2 | 12/2015 | Allen | |
| 9,320,846 B2 | 4/2016 | Burns et al. | |
| 9,433,381 B2 | 9/2016 | Mohl et al. | |
| 9,433,761 B2 | 9/2016 | Schwartz et al. | |
| 9,550,046 B1 | 1/2017 | Allen et al. | |
| 9,844,383 B2 | 12/2017 | Allen | |
| 9,855,049 B2 | 1/2018 | Schiemanck et al. | |
| 9,999,718 B2 | 6/2018 | Brady et al. | |
| 10,118,016 B2 | 11/2018 | Schwartz et al. | |
| 10,315,016 B2 | 6/2019 | Schwartz et al. | |
| 10,952,883 B2 | 3/2021 | Hoem et al. | |
| 11,135,408 B2 | 10/2021 | Schwartz et al. | |
| 2001/0041862 A1 | 11/2001 | Glickman | |
| 2004/0260333 A1 | 12/2004 | Dubrul et al. | |
| 2005/0049451 A1 | 3/2005 | Schock et al. | |
| 2005/0245894 A1 | 11/2005 | Zadno-Azizi | |
| 2005/0245897 A1 | 11/2005 | Bolduc et al. | |
| 2005/0267561 A1 | 12/2005 | Jones et al. | |
| 2008/0300573 A1 | 12/2008 | Consigny et al. | |
| 2009/0177183 A1 | 7/2009 | Pinkernell et al. | |
| 2010/0168649 A1 | 7/2010 | Schwartz et al. | |
| 2010/0249704 A1 | 9/2010 | Wagner | |
| 2010/0280451 A1 | 11/2010 | Teeslink et al. | |
| 2011/0196255 A1 | 8/2011 | Kassab | |
| 2012/0157913 A1 | 6/2012 | Aziz et al. | |
| 2012/0265079 A1 | 10/2012 | Hilmersson | |
| 2012/0265283 A1 | 10/2012 | Mack et al. | |
| 2013/0035560 A1 | 2/2013 | Anand et al. | |
| 2013/0165858 A1 | 6/2013 | Cox et al. | |
| 2015/0133799 A1* | 5/2015 | O'Connell | A61B 5/0215 600/486 |
| 2015/0141853 A1 | 5/2015 | Miller, III et al. | |
| 2016/0082178 A1 | 3/2016 | Agah et al. | |
| 2016/0199003 A1 | 7/2016 | McCaffrey et al. | |
| 2016/0213834 A1 | 7/2016 | Brady et al. | |
| 2016/0270731 A1 | 9/2016 | Burkett | |
| 2016/0361068 A1 | 12/2016 | Mohl et al. | |
| 2017/0189654 A1 | 7/2017 | Schwartz et al. | |
| 2017/0290598 A1 | 10/2017 | Culbert et al. | |
| 2018/0185576 A1 | 7/2018 | Burns et al. | |
| 2018/0280172 A1 | 10/2018 | Hoem et al. | |
| 2018/0353681 A1 | 12/2018 | Burmaster et al. | |
| 2019/0046760 A1 | 2/2019 | Schwartz et al. | |
| 2019/0082976 A1 | 3/2019 | Hoem et al. | |
| 2019/0275248 A1 | 9/2019 | Schwartz et al. | |
| 2019/0358437 A1 | 11/2019 | Schwartz et al. | |
| 2020/0093991 A1 | 3/2020 | Schwartz et al. | |
| 2020/0282189 A1 | 9/2020 | Gaynor | |
| 2020/0383688 A1* | 12/2020 | Olson | A61M 25/10181 |
| 2021/0228387 A1 | 7/2021 | Hoem et al. | |
| 2021/0361170 A1 | 11/2021 | Schwartz et al. | |
| 2021/0366620 A1 | 11/2021 | Bernard et al. | |

FOREIGN PATENT DOCUMENTS

| | | | |
|---|---|---|---|
| CN | 201058169 Y | 5/2008 | |
| CN | 103826690 A | 5/2014 | |
| CN | 108778149 A | 11/2018 | |
| EP | 3399923 A1 | 11/2018 | |
| EP | 3399923 A4 | 8/2019 | |
| GB | 2541368 A * | 2/2017 | A61B 5/021 |
| JP | 2006187620 A | 7/2006 | |
| JP | 2013146505 A | 8/2013 | |
| JP | 2016168151 A | 9/2016 | |
| WO | WO-9600596 A1 | 1/1996 | |
| WO | WO-0128419 A2 * | 4/2001 | A61B 5/0255 |
| WO | WO-0170325 A2 | 9/2001 | |
| WO | WO-2004062526 A2 * | 7/2004 | A61B 5/02007 |
| WO | WO-2006059317 A1 | 6/2006 | |
| WO | WO-2008088579 A2 | 7/2008 | |
| WO | WO-2014106158 A1 | 7/2014 | |
| WO | WO-2015108928 A1 | 7/2015 | |
| WO | WO-2017004432 A1 | 1/2017 | |
| WO | WO-2017078693 A1 * | 5/2017 | A61B 5/02158 |
| WO | WO-2017120229 A1 | 7/2017 | |
| WO | WO-2017160270 A1 | 9/2017 | |
| WO | WO-2018175485 A1 | 9/2018 | |
| WO | WO-2019060421 A1 | 3/2019 | |
| WO | WO-2019173758 A1 | 9/2019 | |
| WO | WO-2019232452 A1 | 12/2019 | |

OTHER PUBLICATIONS

Extended European Search Report dated Jul. 19, 2019 in EP Patent Appl. Serial No. 17736254.8 (0130).
International Search Report & Written Opinion dated Apr. 7, 2022 in Int'l PCT Patent Appl. Serial No. PCT/IB2022/050152 (0810).
International Search Report & Written Opinion dated Aug. 9, 2021 in Int'l PCT Patent Appl. Serial No. PCT/IB2021/054453 (0710).
International Search Report and Written Opinion dated Jan. 3, 2019 in Int'l PCT Patent Application Serial No. PCT/US2018/051760 (0310).
International Search Report and Written Opinion dated Mar. 17, 2017 in Int'l PCT Patent Application Serial No. PCT/US2017/012181 (0110).
International Search Report and Written Opinion dated May 25, 2018 in Int'l PCT Patent Application Serial No. PCT/US2018/023422 (0210).
International Search Report and Written Opinion dated Jul. 3, 2019 in Int'l PCT Patent Application Serial No. PCT/US2019/021426 (0410).
International Search Report and Written Opinion dated Oct. 1, 2019 in Int'l PCT Patent Application Serial No. PCT/US2019/035020 (0510).
International Search Report and Written Opinion dated Nov. 27, 2019 in Int'l PCT Patent Application Serial No. PCT/US2019/052245 (0610).
Lindsey, et al., "Guidelines for Experimental Models of Myocardial Ischemia and Infarction," American Journal of Physiology—Heart and Circulatory Physiology, 314(4):H812-H838 (Apr. 2018).
Liu, JingHua, Coronary Heart Disease: Anatomy, Function and Imaging, Peking Union Medical College Press, Apr. 30, 2013, p. 56.
Qiu, et al., "Microvasculature-on-a-Chip for the Long-term Study of Endothelial Barrier Dysfunction and Microvascular Obstruction in Disease," Nature Biomedical Engineering, 2(6):453-463 (Apr. 2018).
Supplementary European Search Report dated Apr. 24, 2020 in EP Patent Appl. Serial No. 18771178.3 (0230).
Tsai, et al., "In Vitro modeling of the microvascular occlusion and thrombosis that occur in hematologic diseases using microfluidic technology," Journal of Clinical Investigation, 122(1):408-418 (Jan. 2012).

* cited by examiner

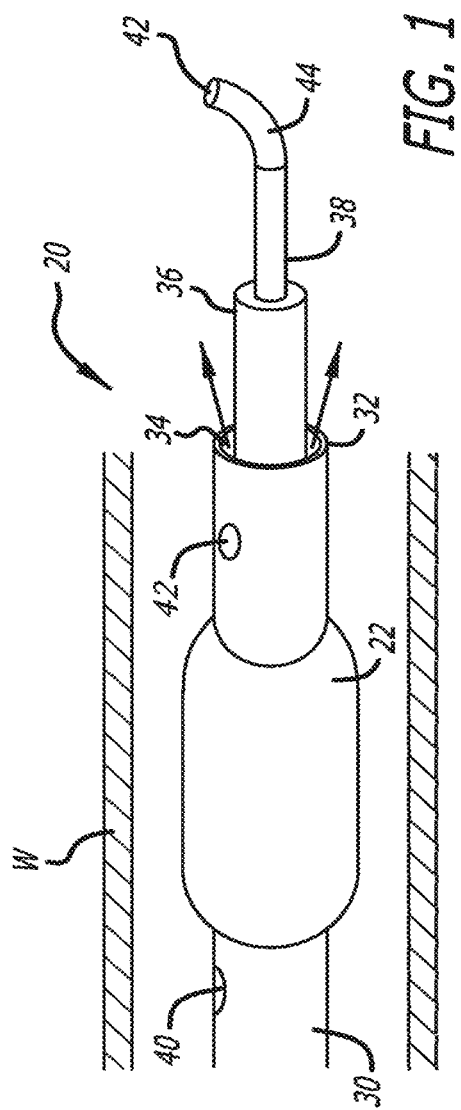
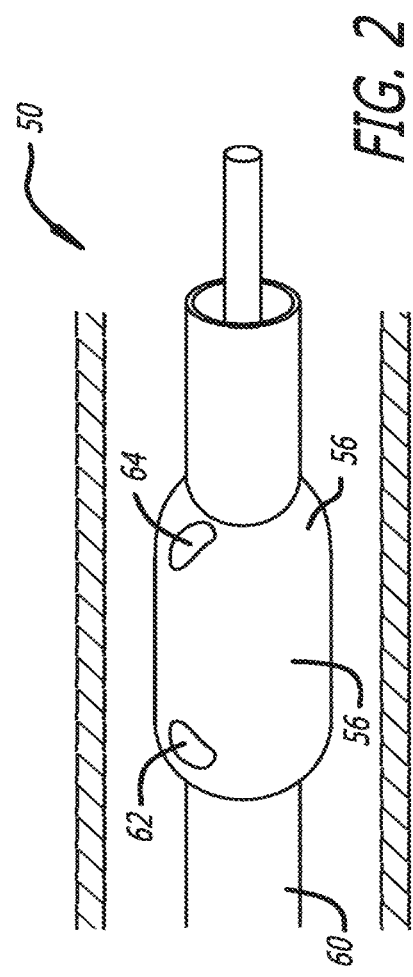

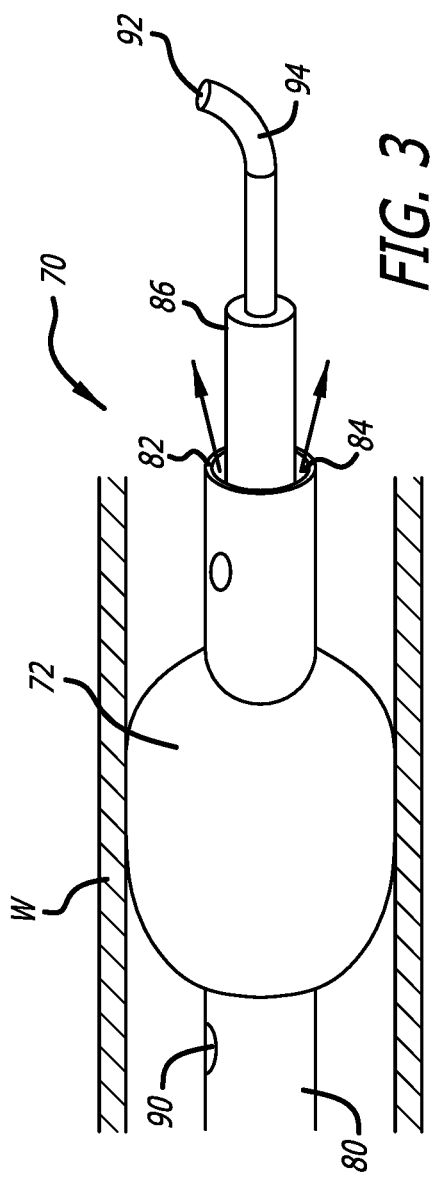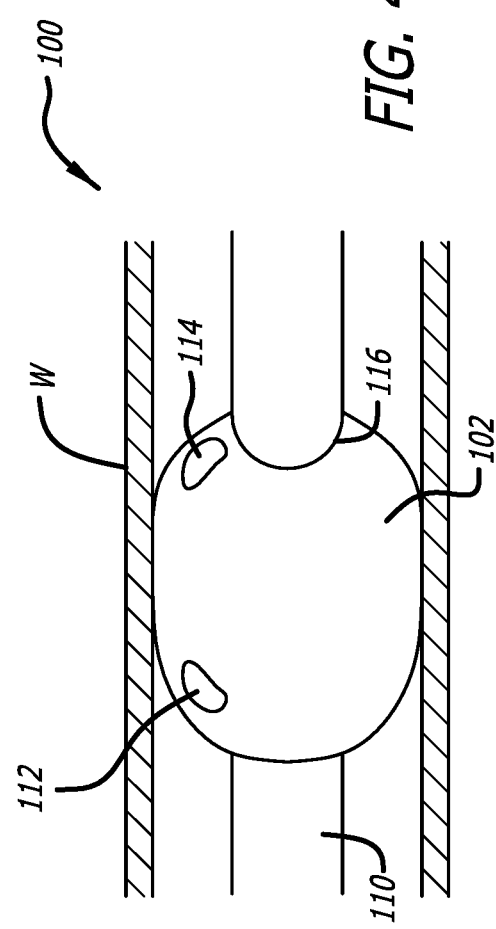

CONTROLLED-FLOW INFUSION CATHETER AND METHOD

RELATED APPLICATIONS

This application claims priority to U.S. Provisional Application Ser. No. 62/889,984 filed Aug. 21, 2019 entitled Controlled Flow Infusion Catheter and Method, which is hereby incorporated herein by reference in its entirety. This application also incorporates by reference the entire contents of U.S. Pat. No. 10,315,016, filed on Jan. 4, 2017 and entitled System and Methods for Treating MVO.

BACKGROUND OF THE INVENTION

Current methods of measuring hemodynamics of a particular blood vessel include thermodilution, Doppler ultrasound, Swan Ganz catheter use involving balloon inflations, and direct pressure measurement. These methods are inadequate in many circumstances because absolute blood flow in volume/time is difficult to accurately measure. Other shortcomings and disadvantages of these methods include potential for operator error and patient trauma. For example, when using catheters with balloon inflation, potential patient trauma can arise from improper balloon inflation techniques and size mismatches to the vessel. Movement artifacts also result in inaccurate data.

There is thus a need for a device and method of precisely measuring blood flow through a specific artery, vein, vessel microvascular network, or organ, or any combination of these in real-time.

OBJECTS AND SUMMARY OF THE INVENTION

The present invention is directed toward devices and methods that satisfy the above-mentioned need. More specifically, the invention is directed to devices and methods that determine various hemodynamic parameters (pressure, flow and resistance) by measuring pressures across suspected lesions or areas of interest.

One aspect of the invention is a method that accurately detects and measures large vessel volume flow in real time without thermodilution, Doppler ultrasound or any other traditional method. An example application is cardiac output measurement without the need for thermodilution, Doppler, or Fick Hb saturation-based flow assessments.

Another aspect of the invention is a method and device that measures coronary artery flow, renal artery flow, pulmonary flow at the segmental level or higher, or any other major organ such as the brain.

Another aspect of the invention is a method or technique that may be used in real-time to monitor patients with heart failure of any cause, such as those that would traditionally be monitored in an intensive care unit (ITU) or coronary care unity (CCU) with pulmonary artery (PA) pressure measurement and or thermodilution cardiac output measurement, such as using a Swan Ganz catheter and bedside unit.

Yet another aspect of the invention provides techniques and devices that can provide continuous or intermittent assessments without catheter balloon inflations, and be free of movement artifacts and balloon inflation operator errors.

Still another aspect of the invention is a technique and device that accurately measures hydraulic resistance of stenosis in any of the above biologic structures, and thus allows the derivation of fractional flow reserve (FFR), index of microvascular resistance (IMR) and coronary flow reserve (CFR) measurements for clinical application.

One aspect of the invention is a method of making real-time determinations of flow resistance through a targeted location in a fluid vessel comprising: placing a distal pressure sensor distal of a targeted location in a fluid vessel; placing a proximal pressure sensor proximal of the targeted location in the fluid vessel; increasing resistance to natural blood flow through the vessel at the targeted location; introducing infusate at an infusate flow rate into the vessel proximal of the distal sensor; changing the infusate flow rate while monitoring pressure differences between the proximal and distal sensors; calculating flow resistance using a measured change in pressure differences in response to the change in infusate flow rate.

In one embodiment of this method, placing said distal pressure sensor distal of the targeted location in the fluid vessel comprises placing a pressure-sensing guide wire distal of the targeted location in the fluid vessel.

In another embodiment of this method, placing said distal pressure sensor distal of the targeted location in the fluid vessel comprises placing a catheter to which said distal pressure sensor is attached at a location such that said distal pressure sensor is distal of the targeted location.

In another embodiment of this method, increasing resistance to natural blood flow through the vessel comprises placing a catheter at the targeted location.

The method may include inflating a balloon on the catheter.

In one embodiment, the step of introducing infusate at an infusate flow rate into the vessel proximal of the distal sensor comprises activating an infusate pump connected to a catheter having an infusate exit port located at the target location proximal of the distal sensor.

One aspect of the invention provides a method of determining flow resistance through a targeted location in a fluid vessel comprising: placing a catheter at a targeted location in a fluid vessel until a distal pressure sensor associated with the catheter is distal of the targeted location and a proximal pressure sensor associated with the catheter is proximal of the targeted location; relaying data from the distal and proximal pressure sensors to a controller associated with a infusate pump in fluid communication with the catheter; and initiating a sequence in which the infusate pump pumps infusate through the catheter into the targeted site at various flow rates while data received from the distal and proximal pressure sensors is used to calculate flow resistance through the targeted location by dividing the change in infusate flow rate created by the infusate pump by a corresponding change in pressure drop between the proximal and distal sensors.

In one embodiment of this method, placing a catheter at a targeted location causes a pressure gradient at the targeted location. The pressure gradient at the targeted location may be increased by inflating a balloon on the catheter.

In one embodiment of the method the distal pressure sensor associated with the catheter is located on a guidewire extending from the catheter.

In one embodiment, the method includes taking an initial pressure reading prior to initiating the sequence.

Another aspect of the invention is a system for determining flow resistance through a targeted location in a fluid vessel comprising: a catheter having an infusate lumen; an infusate pump connected to the infusate lumen and having a supply of infusate; a controller associated with the infusate pump; a distal pressure sensor associated with the catheter; a proximal pressure sensor associated with the catheter; and a processor that receives data from the distal sensor and the proximal sensor and calculates flow resistance through the targeted location by comparing changes in a pressure gradient across the targeted location as measured by the distal and proximal sensors as infusate flow created by the infusate pump changes.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

FIG. 1 is a perspective view of an embodiment of a device of the invention;

FIG. 2 is a perspective view of an embodiment of a device of the invention;

FIG. 3 is a perspective view of an embodiment of a device of the invention;

FIG. 4 is a perspective view of an embodiment of a device of the invention;

DESCRIPTION OF EMBODIMENTS

Figure 5:
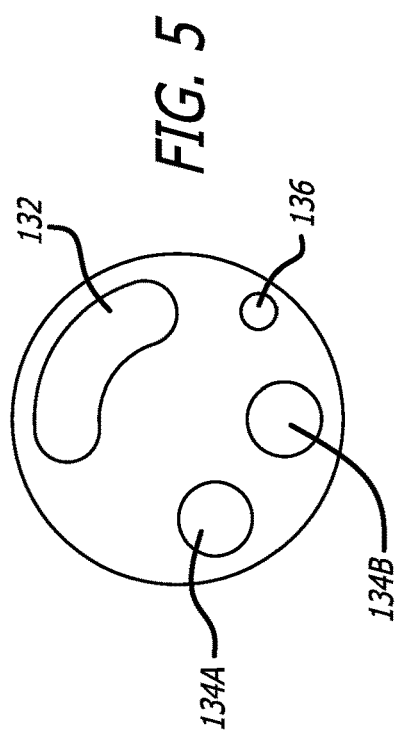
FIG. 5 is an end view of an embodiment of a catheter of the invention showing the lumens and/or channels of the catheter.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention is directed to devices and methods for measuring blood flow, absolute pressure, and blood pressure gradients in any artery, vein, vessel, microvascular network, organ, or combination thereof, in the body. These methods and devices provide data needed to derive such clinically applicable measurements as fractional flow reserve (FFR), index of microvascular resistance (IMR) and coronary flow reserve (CFR), for example.

Various embodiments of devices and methods are described herein that are all drawn to the spirit of the invention. For clarity and organization, attention will first be drawn to a description of the features of the various devices, and generally how they function, and then a more detailed discussion of the use of the devices will be explained in the method section.

Devices

The devices of the invention can be categorized as balloon devices and non-balloon devices. The balloon devices can be further categorized as lumen occluding and lumen non-occluding. The devices include infusion lumens capable of conducting any fluid through partial or complete length of the device, as will be shown in greater detail below, that permit flow infusion from catheters at distal sites in a safe fashion. Controlled flow infusion, such as by a controlled pump—digital or otherwise, is distinct from pressure-based infusion. Controlled flow infusion has volumetric flow set at a defined level or programmed from multiple levels at desired functions of time. The infusion may change in discrete steps or be a continuous function change, either increasing or decreasing.

By comparison, pressure-based infusion entails pressure set by an external pressure source, and flow is permitted to vary based on distal vessel resistance defined by the distal vessel bed vascular resistance using flow, pressure or other means to monitor and control flow.

Balloon Devices

Referring now to the Figures, and first to FIG. 1, there is shown an embodiment of a controlled-flow infusion "CoFI" balloon catheter device 20. The device 20 includes a balloon 22 and a catheter 30. The catheter 30 includes a plurality of channels or lumens. A first channel 32, is a perfusion flow channel, that permits highly-controlled flow to exit from the point in the catheter at which a flow exit is desired. The perfusion flow channel runs the length of the catheter and allows the delivery of an agent, such as a therapeutic or diagnostic agent—for example adenosine, at a location distal of a suspected stenosis or lesion. In FIG. 1, the exit point 34 is located at or proximal of a distal tip 36 of the catheter 30. A second channel 38 is a guidewire lumen and is usable to guide the device 20 over a guidewire 44, which may be a pressure-sensing wire or may be replaced by a pressure-sensing wire after the navigation is complete. The guidewire lumen 38 may extend to the proximal end and be used in an over-the-wire (OTW) fashion or may be in the form of a rapid exchange (Rx) configuration. An inflation lumen (not shown) is integrated into the catheter 30 and is usable to inflate and deflate the balloon 22.

The device 20 of FIG. 1 is shown as having a non-occluding (or partially-occluding) balloon 22, as there is room for fluid flow between the balloon 22 and the vessel walls W. This may be accomplished by either providing a balloon 22 that is smaller than the targeted vessel, or by under-, or partially inflating the balloon 22. An undersized balloon 22 provides the advantage of being able to tactilely inflate until resistance indicates that the balloon is full. However, care would have to be taken to ensure that the balloon is correctly sized and that inadvertent occlusion does not occur, if undesired. Underinflating a balloon provides the advantage of being able to use the same balloon in various locations, so long as care is taken not to overinflate.

Device 20 further includes a proximal pressure sensor 40 and a distal pressure sensor 42. The proximal pressure sensor 40 is located on the catheter 30 proximal of the balloon 22, but may alternatively be mounted on the balloon 22. The distal pressure sensor 42 may be located on the catheter 30 distal of the balloon 22, or it may be located near the distal end of a guidewire 44. Two distal pressure sensors 42 are shown in FIG. 1, one on the catheter and one on the distal end of the guidewire 44. This duplicative depiction of the distal sensor 42 is only for illustrative and explanatory purposes to show the various locations. This depiction should not be interpreted as the invention requiring more than one distal pressure sensor. Additionally, the distal pressure sensor may alternatively be mounted on a distal end of the balloon 22, as shown in FIG. 2.

The device 50 of FIG. 2 is an alternative non-occluding or partially-occluding balloon design. The device 50 includes a balloon 52 and a catheter 60. Like the device 20 of FIG. 1, the device 50 of FIG. 2 includes a proximal pressure sensor 62 and a distal pressure sensor 64, however these sensors are located on the balloon 52 instead of on the catheter. The proximal pressure sensor 62 is located near a proximal end 54 of the balloon 52 and the distal pressure sensor 64 is located near a distal end 56 of the balloon 52. An inflation lumen (not shown) is integrated into the catheter 60 and is usable to inflate and deflate the balloon 52. The locations of the proximal and distal sensors are not reliant on each other. Thus, one of the sensors may be located on the balloon while the other is located on the catheter or on a guidewire.

The non-obstructing configurations can be used to generate a gradient across the balloon, with the gradient being measured by the sensors and proportional to flow. Measures of pressure, resistance, and flows can be facilitated with the balloon, though the use of the balloon is not mandatory for diagnosis. The balloon is optional for diagnostics, but also enhances therapeutic delivery to distal occluded channels, including macro- and/or microvascular obstructions. Typically, the balloon configured in this fashion does not necessarily occlude the vessel to provide the ability to increase distal pressure as flow is infused via the integral catheter perfusion channels, providing a distinct therapeutic advantage over the non-balloon configurations. The infusate may be simple biocompatible liquids such as normal saline, dextrose saline, Ringer's lactate or other therapeutic agents such as anti-thrombotics, vasodilators or others.

These embodiments will permit accurate pressure, flow, microvascular or macro-resistance measures or derivations either with or without partial or complete catheter obstruction using an intentionally mildly obstructing device such as a balloon, or the completely non-obstructing embodiments described below if no proximal resistance is desired.

FIGS. 3 and 4 show similar devices to those of FIGS. 1 and 2, respectively, except that these devices include occluding balloons instead of non-occluding balloons. The device 70 of FIG. 3 includes a balloon 72 and a catheter 80. The catheter 80 includes a plurality of channels or lumens. A first channel 82, is a perfusion flow channel, that permits highly-controlled flow to exit from the point in the catheter at which a flow exit is desired. The perfusion flow channel runs the length of the catheter and allows the delivery of an agent, such as a therapeutic or diagnostic agent—for example adenosine, at a location distal of a suspected stenosis or lesion. In FIG. 3, the exit point 84 is located at or proximal of a distal tip 86 of the catheter 80. An inflation lumen (not shown) is integrated into the catheter 80 and is usable to inflate and deflate the balloon 72.

Device 70 further includes a proximal pressure sensor 90 and a distal pressure sensor 92. The proximal pressure sensor 90 is located on the catheter 80 proximal of the balloon 72. The distal pressure sensor 92 may be located on the catheter 80 distal of the balloon 72, or it may be located near the distal end of a guidewire 94, as shown. Two distal pressure sensors 92 are shown in FIG. 3, one on the catheter and one on the distal end of the guidewire 94. This duplicative depiction of the distal sensor 92 is only for illustrative and explanatory purposes to show the various locations. This depiction should not be interpreted as the invention requiring more than one distal pressure sensor. Additionally, the distal pressure sensor may alternatively be mounted on a distal end of the balloon 72, as shown in FIG. 4.

The device 100 of FIG. 4 is an alternative non-occluding balloon design. The device 100 includes a balloon 102 and a catheter 110. Like the device 70 of FIG. 3, the device 100 of FIG. 4 includes a proximal pressure sensor 112 and a distal pressure sensor 114, however these sensors are located on the balloon 102 instead of on the catheter. The proximal pressure sensor 112 is located near a proximal end 104 of the balloon 102 and the distal pressure sensor 114 is located near a distal end 116 of the balloon 102. An inflation lumen (not shown) is integrated into the catheter 1100 and is usable to inflate and deflate the balloon 102. The locations of the proximal and distal sensors are not reliant on each other. Thus, one of the sensors may be located on the balloon while the other is located on the catheter or on a guidewire.

The aforementioned balloons, whether occlusive or non-occlusive (partially occlusive) have both diagnostic and therapeutic uses. Diagnostically, they are used to occlude, either partially or completely, the vessel proximal to a location in which resistance is to be assessed. Therapeutically, the balloons provide a proximal occlusion, which prevents retrograde flow of the infused therapeutic fluid. The balloon thus acts as a backstop from which infusion pressures may be generated and more effectively deliver agents to the distal vascular beds. Doing so markedly enhances forward, antegrade therapeutic agent flow into distal microvessels (partially or completely occluded).

FIG. 5 shows a cross-sectional view of any or all of the catheter designs mentioned herein, provided to show catheter lumen configurations. As explained above, there is a perfusion flow channel 132 (32 in FIGS. 1 and 82 in FIG. 3). Also shown are fluid-filled channels 134A and 134B. These fluid-filled channels 134 allow fluid pressure measurement either via pressure sensors or pressure-sensing guidewires which can be placed and maneuvered as needed to obtain accurate pressures. Fluid within the channels conduct pressure to the proximal ports of the balloon, and external, standard fluid pressure sensors can measure proximal pressures. These channels 134 may thus contain one or multiple pressure-sensing guidewires, or be adapted for fluid pressure measurement, such as with the incorporation of sensors. The use of fluid channels would allow pressure measurements to be taken external to the wire at specific sites within the catheter. Also shown is an inflation lumen 136 for a balloon.

Figure 6:
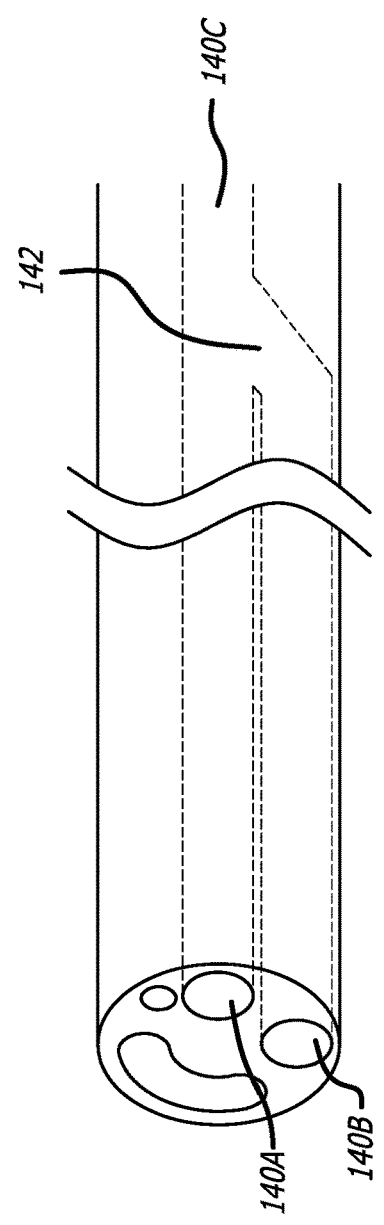
FIG. 6 is a perspective view of an embodiment of a catheter of the invention with internal lumens and/or channels shown in phantom lines.

The catheter designs may also include a hybrid lumen 140 that provides an ability to use a guidewire to deliver catheter in a rapid-exchange (Rx) configuration remove and exchange the wire for a pressure wire that will enable pressure sensing at that distal site. The hybrid lumen 140 is further depicted in FIG. 6 and shows two branches 140A and 140B converging into a single lumen 140C (collectively referred to as hybrid lumen 140).

The hybrid lumen 140 may be formed by connecting an Rx skive to an inner lumen. The Rx skive would then serve as one of the branches 140A or 140B. Thus, if the Rx skive served as branch 140B, for example, the hybrid lumen 140 would include a first lumen that extends from the proximal end to the distal end of the catheter and an Rx skive 140B that joins the first lumen to form an intersection 142, and defines the boundaries of branches 140A, 140B, and 140C, in which the first lumen forms branch 140A from the proximal end to the intersection 142, at which point it continues distally as branch 140C.

A delivery catheter with a hybrid lumen 140 may thus be used as a dual function catheter in the same procedure. In one role, the catheter serves as an Rx catheter. In another role, the hybrid lumen (140A combined with 140C) allows the catheter to function as an over-the-wire (OTW) catheter.

With the Rx skive 140B connected to the inner lumen 140A-C, the catheter is capable of removal via the Rx configured lumen. Thus, the lumen 140B does not extend internally from the intersection to the proximal end of the catheter like 140A. Rather, lumen 140B exits the catheter prior to reaching the proximal end, though it may have a connection path to the proximal catheter port. The hybrid Rx-OTW dual function capacity also permits the use of a standard, off-the-shelf percutaneous coronary intervention (PCI) guidewire for a therapeutic procedure in the Rx mode, followed by exchanging for a pressure wire to perform resistance and/or flow measurements using the methods described herein.

For example, a standard PCI wire could be used to guide a procedure, such as stenting or balloon angioplasty, in a usual fashion. Once the procedure is complete, the catheter used in the procedure is removed, leaving the Rx PCI wire in place. A catheter of the invention is then routed over the guidewire using the hybrid lumen 140, leaving other guidewire channels open for either pressure measurement or guidance.

Figure 7:
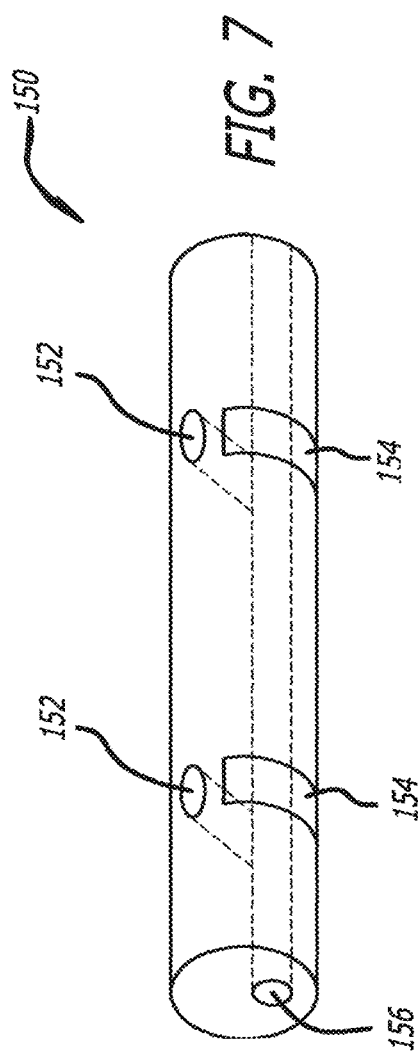
FIG. 7 is a perspective view of an embodiment of a catheter of the invention with internal lumens and/or channels shown in phantom lines.

FIG. 7 shows an embodiment of a catheter body 150, which includes a multiplicity of sites 152 along the longitudinal length of the catheter body. This catheter body 150 may be used with any or all of the above catheter devices. The sites 152 are characterized by connections between an interior lumen 156 (such as those described above) and an exterior of the catheter 150. These connections may be in the form of holes, slits, slots, ports, skives, or other geometrically configured connections. These connections may be cut or otherwise formed into the catheter. Additionally, markers 154 (radiopaque or otherwise) may be included on the catheter body 150 to mark the locations of these connections. Pressure sensing guidewires can also be used in any of these configurations.

In use, an embodiment of a catheter of the invention having a catheter body 150 is delivered to the desired site by aligning one of the hole connections 152 at the site, and then delivering a pressure-sensing wire to the location of the hole 152. Contamination across sites is prevented since the guidewire channel is close to the size of the guidewire itself, thus blocking pressure contamination from proximal or distal connection sites 152.

Figure 8:
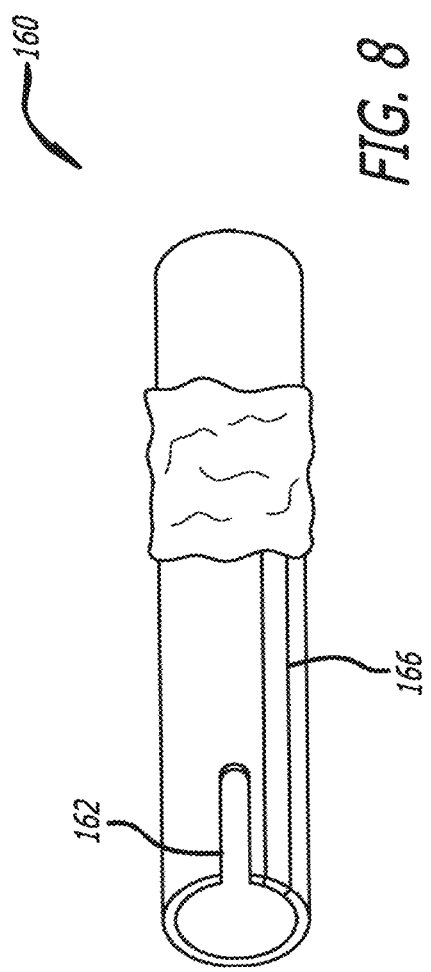
FIG. 8 is a perspective view of an embodiment of a device of the invention.

FIG. 8 shows an embodiment 160 of a balloon catheter that has an attachment mechanism 162, such as a slot or other connector, that allows the balloon 164 and its infusion lumen 166 to be attached to another catheter or wire and delivered to the distal site of the catheter or wire. This is configured as an Rx device, where the balloon is attached to the catheter and guided to the local distal site. In FIG. 8, the attachment mechanism 162 is in the form of a slot that allows the proximal end of the catheter 160 to expand over the distal end of another catheter. Alternatively, other telescoping or end to end connection mechanism could be employed including, but not limited to, elastic materials, bands, threads, luer locks, clamps, and the like.

Non-Balloon Devices

Figure 9:
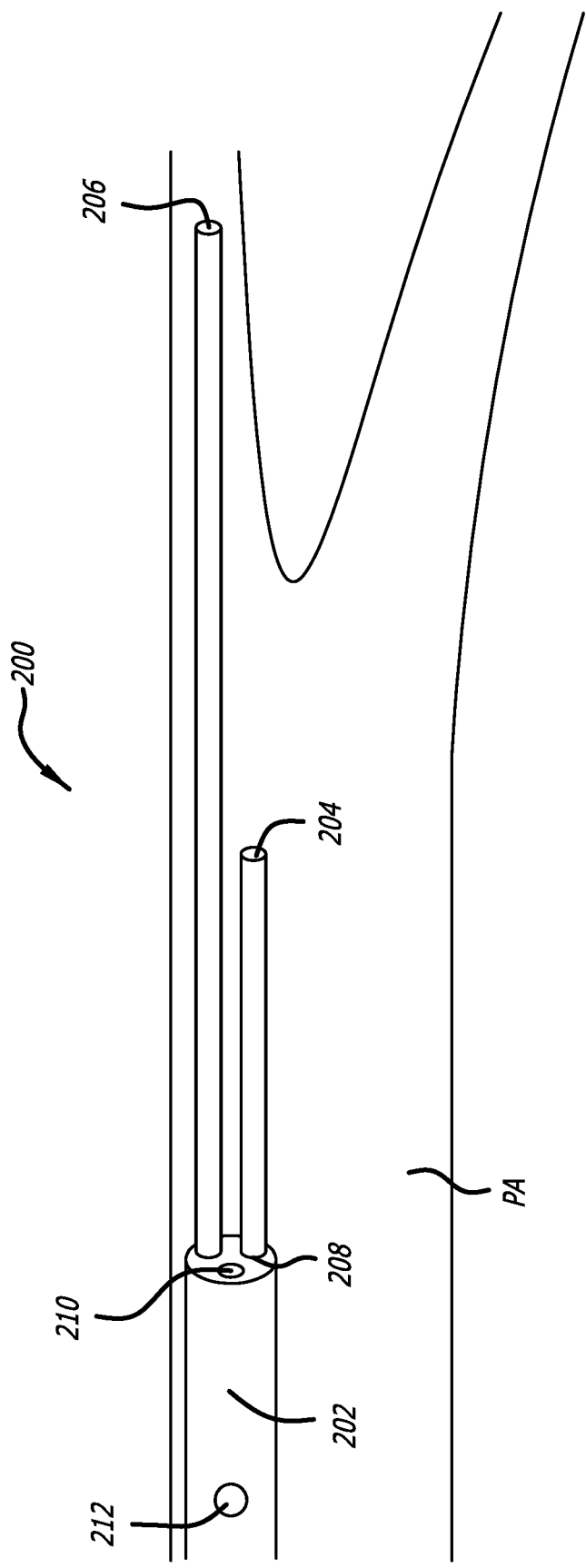
FIG. 9 is a perspective view of an embodiment of a device of the invention.

FIG. 9 shows a catheter device 200 that does not utilize a balloon. The device 200 includes a catheter body 202 (which may be identical to catheter body 150) and proximal and distal pressure sensors 204 and 206, respectively. The catheter body 202 includes one or more guidewire channels 208, and may further include fluid-filled channels 210.

The pressure sensors 204, 206 or both, may be mounted on an exterior surface of the catheter body 202 or they may be deployed on one or more guidewires or probes to be routed through hole connections 212 of the catheter body 202. Having at least one sensor associated with a guidewire or probe may provide additional flexibility in terms of where pressure readings are to be taken, and the distance between the proximal and distal sensors 204 and 206. As seen in FIG. 9, this embodiment may be particularly useful when it is desired that the distal sensor 206 take a measurement in a segmental or sub-segmental vessel, while the proximal sensor 204 remains in a major artery such as the pulmonary artery PA.

Figure 11:
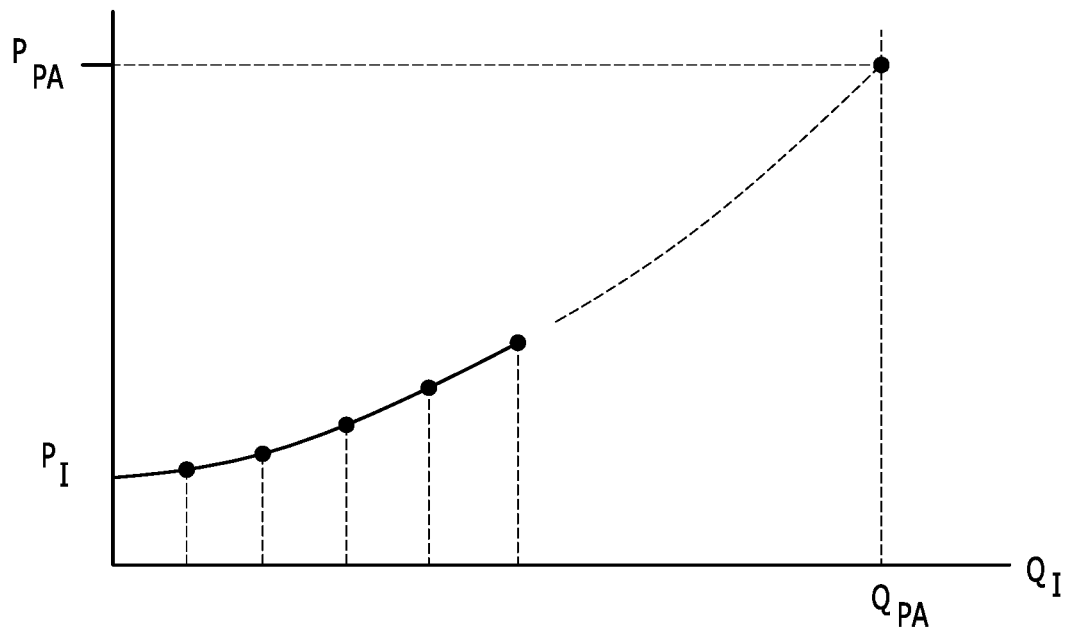
FIG. 11 is a graph showing an extrapolation of information based on five infusate pressure readings.

Resistance Measurement Methods:

Generally, fluid volume flow is infused into the catheter at changing but defined rates for defined time periods. The fluid volume flow may be crystalloid, saline, blood or other flow agents. These defined time periods will typically be about 15 seconds or longer per period. A typical flow sequence will be a step function, either increasing or decreasing. The resistance is then calculated by deriving the infusate Q-P linear regression using slope and intercept. Pressure sensing is either integrated into the catheter or is provided by sensors located on guidewires, or may be provided by other monitoring methods. The graph of FIG. 11 shows the extrapolation of information based on 5 infusate pressure readings ($P_I$) taken at different known infusate flow rates ($Q_I$), denoted by the data points and the vertical dotted lines leading from the data points to the x-axis. The intercept is determined by taking a pressure reading prior to performing the procedure, when infusate flow ($Q_I$) is zero. $Q_{PA}$ is the ambient flow rate in the pulmonary artery when pressure in the pulmonary artery $P_{PA}$ is to be measured.

If no balloon is used, the flow interacts with distal vascular bed pressure and a gradient develops. This is measured by one or more pressure sensing mechanisms described above (e.g. pressure sensors on the catheters or on the guidewires). The distal pressure developed in response to flow is proportional to resistance.

If a balloon is used, the balloon partially or completely obstructs flow and fluid flow (ringer, saline, blood, etc.) is infused through the distal infusion port. The pressure $P_1$ proximal to the balloon or obstruction is measured as is the pressure $P_2$ distal to the balloon or obstruction. The mathematical pressure difference is taken and is defined as they gradient across the obstruction. The graph of FIG. 12 shows the relationship between the difference of distal pressure $P_2$ and proximal pressure $P_1$, in relation to infusate flow $Q_I$.

Figure 12:
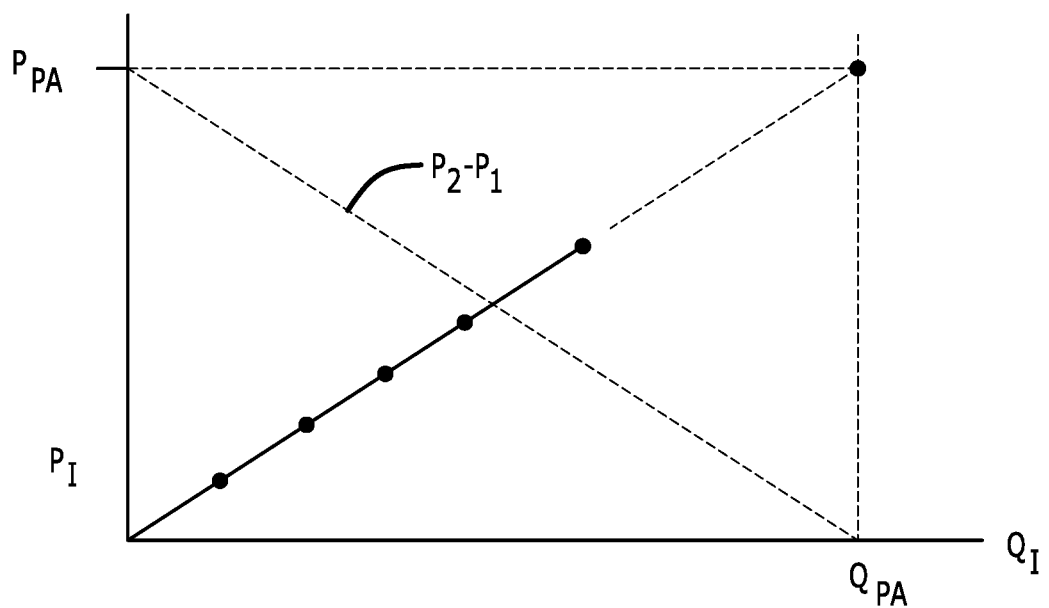
FIG. 12 is a graph showing the relationship between the difference of distal pressure and proximal pressure in relation to infusate flow; and, FIG. 13 is a graph showing how the derivative of dP/dQ can be used to calculate the instantaneous resistance at any given infusate flow rate.

The graph of FIG. 12 shows that after the occlusion balloon is inflated but before infusate flow has begun (QI=0), the difference between the pressure at the proximal sensor P2 and the pressure at the distal sensor P1, is at a maximum. As the infusate flow QI is raised, the pressure builds on the distal sensor P1 while the proximal sensor P2 is isolated from the infusate flow, and thus does not change. As such, P2−P1 decreases as infusate flow increases. Once the difference in pressures reaches zero, the infusate flow rate is noted as it necessarily equals QPA. At this point, pulmonary resistance RPA can be calculated by dividing the measured pulmonary pressure, PPA by the pulmonary flow rate QPA.

Figure 13:
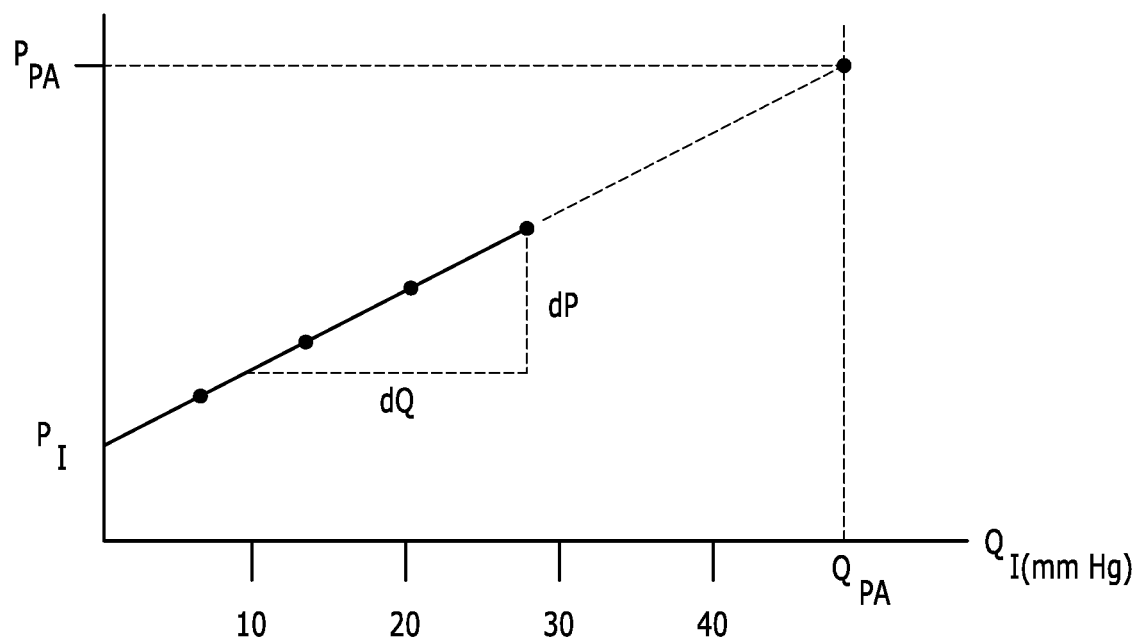

The graph of FIG. 13 shows how the derivative dP/dQ can then be used to calculate the instantaneous resistance at any given infusate flow rate $Q_I$.

The devices and methods of the present invention vary based on scenario and, as such, are best described by providing examples:

Example 1

In this example, the intended application is as follows: A diagnostic CoFI catheter is being used that allows the operator to utilize any conventional coronary guidewire for PCI, after which a pressure wire will be routed to the distal site using guidewire exchange (pressure wire for PCI wire). The pressure wire will be then used for distal pressure measurement, flow infusion, and therapeutic infusion capabilities.

The following sequence exemplifies a method of this invention given these circumstances:

First the PCI procedure is initiated by guide catheter placement and an interventional stent/balloon catheter is delivered using a commercial guidewire of choice.

Next the therapeutic procedure is completed successfully with stent placement and post-dilatation. The commercial guidewire is left in place, and an Rx stent catheter is removed when the operator is satisfied with stent placement.

Next a CoFI diagnostic catheter is inserted using a dual channel-connecting guidewire dual-lumen channel and is delivered distally to the interventional site.

The commercial guidewire is then removed from the dual channel lumen at the Rx proximal skive, leaving a core catheter in place with no guidewires. A distal pressure sensing guidewire is inserted into the dual lumen (Rx-OTW) and exits at the distal end, providing distal pressure measurements beyond the interventional site.

The proximal pressure guidewire is next delivered through lumen number two to a desired proximal site. This leaves a perfusion-capable catheter in place with two pressure sensors spaced apart longitudinally.

Next the operability of both pressure sensors are verified electronically and are deemed ready to record proximal and distal pressures.

Infusion then begins through the infusion lumen at typical controlled step function flow infusion levels (eg 5, 10, 20, 30, 40 mL/min) or an arbitrary volume flow function.

Data is collected and processed from this combination that permits the determination of CoFI flow-pressure relationships.

Next, flow sequencing is developed. A standard CoFI step function is used to generate flow-pressure relationship: computer or digital controlled or accurately known flow source infusing physiologic solution such as saline Ringer's lactate blood substitute plasma or other compatible liquid.

Next, the calculations to determine the infusate flow-pressure relationships are completed as follows:

Extrapolate Qmax and Pmax and calculate P1−P2 gradient;

Find Qmax at which P1−P2=0, or alternatively when P1=proximal pressure (Aorta or Main PA), typically linear;

Derive the slope and intercept of the linear flow-pressure relationship;

Measure proximal pressure when infused flow is zero;

Use the flow-pressure linear relationship to calculate a flow point at which inserted pressure equals P0, or proximal zero flow pressure;

Exact resistance is then calculated as Pq/Q0. In cases of phasic flow, mean value or RMS values may be utilized.

A specific real-world application of Example 1 may involve the lungs or pulmonary microvascular bed, such as when testing for microvascular response to hypoxia or pressure stimuli or other pressure or flow modifying agents or maneuvers.

In this case, the stimulus used would be graded hypoxia/low oxygen tension, and this would be accomplished by having the patient hold their breath while monitoring saturation.

Using the devices of the invention, one next measures pressure and flow relationships as blood oxygen saturation changes.

Low FIO2: oxygen tension: breathe gasses of varied oxygen concentrations by mixing oxygen with another neutral, harmless gas such as helium or nitrogen, for example.

Next, the pulmonary capillary response function is determined. This function is most likely linear and can be determined using the P/Q formulation at $P_1−P_2=0$. The instantaneous resistance is calculated as the derivative dP/dQ.

This method has several applications, such as measuring microvascular resistance to determine a likelihood of successful treatment for a variety of therapies including, but not limited to, pharmacologic, shunt, and impedance matching, and determining the potential for success by assessing the residual microvascular responsivity. A large dP/dQ could indicate high responsiveness and thus likely treatment success.

Example 2—Small, Accurate Real-Time Measurements

In this example, a case presents itself involving a location that requires small, accurate real-time flow measures, such as a segmental or sub segmental artery in the lung. This is advantageous to determine location and severity of pulmonary (or other organ, e.g. brain, kidney, peripheral vessels etc.) vasomotor dysfunction.

In this example, one would use mathematical extrapolation of CoFI pressure-flow relationships, obtaining $P_{PA}$ from $Q_{PA}$ and thus permits a direct P/Q resistance calculation. This provides the following advantages/capabilities:

1) Quotient P/Q at zero gradient
2) Diagnostic
3) Multiple headed device to simultaneously measure different vessels
4) Segmental/subsegmental
5) Place catheter/balloon at local site
6) Allows measurement at any site at the vessel
7) Not achievable with any other technique
8) Can be used at any point in vessel or branch

Example 3—Therapeutic Catheter Applications

Pulmonary/internal lung elastance causes capillary collapse at low flow rates. This creates VQ mismatch and may be treated by hydrodynamic means. Pressurized fluid (compatible) from the pulmonary artery CoFI pump results in capillary expansion. Additionally, pharmacotherapy for spasm, thrombus and intima could be used. Such agents include vasodilators (NO active, Prostacyclin analogs, Endothelin receptor antagonists).

The procedures may be repeated in a patient on a regular basis, and the above devices and methods with thus be serially used with resulting 1) measures of success or failure, 2) initially determining whether a particular patient is likely to respond.

Example 4—Poor O2 Saturation

This example discusses the diagnostic options from the above system in patients with poor oxygen saturation centrally or peripherally. The above system provides the following advantages and capabilities:

Diagnose and treat with same device immediately.

Shunts and V-Q mismatches—where, how severe, response to therapy

Determines flow even in small vessels by utilizing different balloon sizing and providing calibrated filling requirements for various balloon sizes.

Example 5—Coronary Measurements

FFR, IFR, CFR and other coronary physiologic measurements can be made using this process. The following sequence of events permit exact measurement of hydraulic resistance in the case of a vascular stenosis. Note that no balloon is required to perform FFR in this fashion.

First, the CoFI catheter is brought proximal to the coronary artery or other vascular stenosis.

Next the distal pressure guidewire exits CoFI catheter and crosses the stenosis.

Fluid perfusion lumen of CoFI catheter is maintained proximal to the stenosis

Pressure guidewire #2 or catheter integral pressure sensor also remains proximal to stenosis.

CoFI fluid infusion begins, and as it rises proximal and distal pressures are measured across the stenosis as a function of controlled antegrade flow.

CoFI fluid has zero oxygen content, so that during flow distal vessel bed is ischemic and dilates fully, resulting from hypoxic vasodilation.

CoFI pressure-flow relationship is established over a series of stepped CoFI flows.

The pressure-flow relationship of the stenosis is now known with no need for vessel occlusion. This function is linear and has a slope m and an intercept b.

Extrapolation of the linear relationship to the point at which antegrade pressure equals systemic pressure (aortic) yields a corresponding flow calculated from the linear relationship $Qc=(Pc-b)/m$.

Hydraulic resistance of the stenosis is the simple expression $Pc/Qc$

Flow measurement without balloon: Volumetric Blood Flow in any vessel, chamber is measured as follows.

Connect CoFI system to catheter and perform standard CoFI flow infusion sequencing.

Obtain Q-P linear relationship slope (m) and intercept (b) parameters.

Measure baseline proximal pressure: pulmonary artery, aorta of any vessel in which flow rate is desired.

Perform calculation for CoFI Flow Q at which CoFI Pressure P is equal to baseline proximal pressure Calculate flow Qpa as the flow at which this pressure is generated.

Quotient Ppa/Qpa is the distal resistance

Above enables real-time flow measurement

Using the Q-P parameters as above.

Real time flow is available from the linear Q-P relationship.

Measured P, calculate Q in real time

Re-Calibrate as necessary

Re-do the CoFI controlled flow infusion to generate and modify the Q-P relationship as needed.

This yields flow Q in real time.

Flow measurement with balloon

The balloon is deployed in a non-occlusive fashion. It thus presents a resistance that generates a back pressure when placed within a flow field. Proximal and distal sensors, either from pressure wires or from sensors on the catheter and integral measure flow dependent gradients across the balloon. As the CoFI diagnostic flow infusion proceeds, flow is measured and known, and the gradient across the balloon is similarly recorded. The distal pressure at the balloon site increases as flow increases, and Pressure-flow relationships between the CoFI flow and the gradient across balloon are linear. The resulting linear equation is solved to find the point where the gradient across the balloon is zero, and as such at this point CoFI volume flow is equal to initial vascular flow, such as cardiac output in the case of a major blood vessel which receives all of the cardiac output. Otherwise, the volume flow in any vessel can be obtained when the trans balloon gradient is either measured as zero as the CoFI volume flow increases or can be solved mathematically by the simple linear equation governing pressure and flow. Once this equation is solved trans balloon pressure can be measured, and this gradient can be translated directly into a volume flow in the short-term.

System

Figure 10:
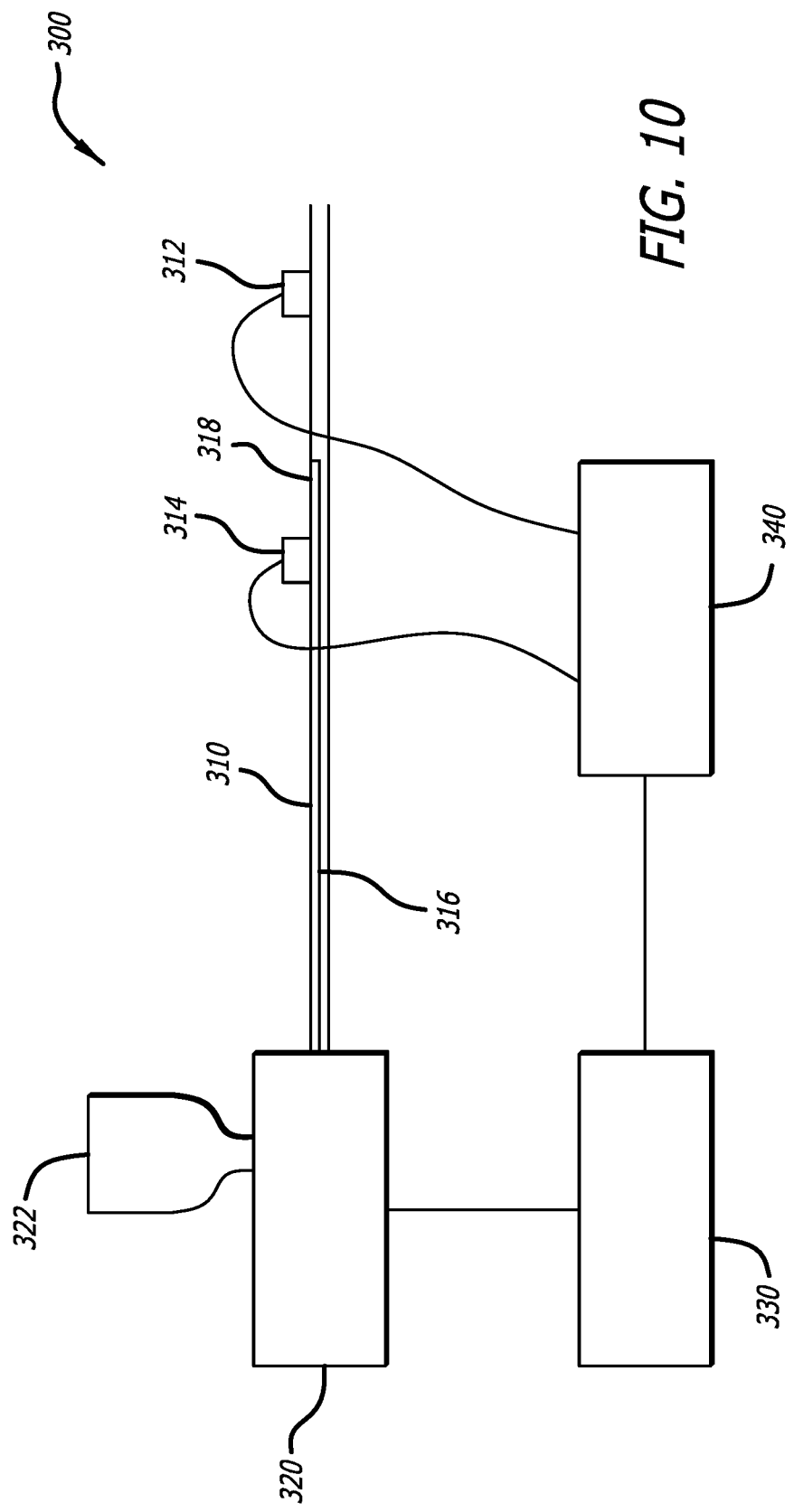
FIG. 10 is a schematic diagram of an embodiment of the system of the invention.

Having described the various device and method embodiments, attention is now drawn to FIG. 10, which shows a schematic diagram of an embodiment of a system 300 of the invention. This schematic diagram is not drawn to scale nor is it meant to depict anything but the associate between the basic components of an embodiment of a system of the invention.

The system 300 generally includes a catheter 310 having a distal pressure sensor 312 and a proximal pressure sensor 314 associated with the catheter as described in any of the embodiments described above. The catheter includes an infusate lumen 316 that is connected to an infusate pump 320 as one skilled in the art would understand. The infusate lumen extends distally to an exit port 318 located between the proximal and distal sensors.

The infusate pump 320 is connected to, or contains, a supply of infusate 322. The infusate pump 320 is associated with a controller 330. The term "associated" is to be interpreted broadly throughout the specification as meaning there is a relationship between the subject components, in this case the controller and the infusate pump, either in a strictly physical sense or in a command-control sense, in that action taken by the controller has an effect on the infusate pump. The term "associated with" can thus be read as meaning connected to, physically or wirelessly, integrated with, embedded in, in data communication with, etc.

The system 300 further includes a processor 340, which may be part of the controller 330, that receives data from the distal sensor 312 and the proximal sensor 314 and calculates flow resistance through the targeted location by comparing changes in a pressure gradient across the targeted location as measured by the distal and proximal sensors 312 and 314 as infusate flow created by the infusate pump changes, according to any of the methods described herein.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of making real-time determinations of flow resistance through a targeted location in a blood vessel comprising:
   placing a distal pressure sensor distal of a targeted location in the blood vessel;
   placing a proximal pressure sensor proximal of the targeted location in the blood vessel;
   introducing infusate at an infusate flow rate into the blood vessel proximal of the distal sensor;
   changing the infusate flow rate while monitoring pressure differences between the proximal and distal sensors;
   calculating flow resistance through the targeted location by dividing the change in pressure drop between the proximal and distal sensors by a corresponding change in the infusate flow rate.

2. The method of claim 1 wherein placing said distal pressure sensor distal of the targeted location in the blood vessel comprises placing a pressure-sensing guide wire distal of the targeted location in the blood vessel.

3. The method of claim 1 wherein placing said distal pressure sensor distal of the targeted location in the blood vessel comprises placing a catheter to which said distal pressure sensor is attached at a location such that said distal pressure sensor is distal of the targeted location.

4. The method of claim 1 further comprising increasing resistance to natural blood flow through the blood vessel by placing a catheter at the targeted location.

5. The method of claim 4 further comprising inflating a balloon on the catheter.

6. The method of claim 1 wherein introducing infusate at an infusate flow rate into the blood vessel proximal of the distal sensor comprises activating an infusate pump connected to a catheter having an infusate exit port located at the target location proximal of the distal sensor.

7. A method of determining flow resistance through a targeted location in a blood vessel comprising:
   placing a catheter at a targeted location in the blood vessel until a distal pressure sensor associated with the catheter is distal of the targeted location and a proximal pressure sensor associated with the catheter is proximal of the targeted location;
   relaying data from the distal and proximal pressure sensors to a controller associated with an infusate pump in fluid communication with the catheter;
   initiating a sequence in which the infusate pump pumps infusate through the catheter into the targeted site at various flow rates while data received from the distal and proximal pressure sensors is used to calculate flow resistance through the targeted location by dividing the change in infusate flow rate created by the infusate pump by a corresponding change in pressure drop between the proximal and distal sensors.

8. The method of claim 7 wherein placing a catheter at a targeted location causes a pressure gradient at the targeted location.

9. The method of claim 8 wherein the pressure gradient at the targeted location is increased by inflating a balloon on the catheter.

10. The method of claim 7 wherein the distal pressure sensor associated with the catheter is located on a guidewire extending from the catheter.

11. The method of claim 9 wherein the distal pressure sensor associated with the catheter is located on the balloon.

12. The method of claim 7 further comprising taking an initial pressure reading prior to initiating the sequence.

13. A system for determining flow resistance through a targeted location in a blood vessel comprising:
   a catheter having an infusate lumen;
   an infusate pump connected to the infusate lumen and having a supply of infusate;
   a controller associated with the infusate pump;
   a distal pressure sensor associated with the catheter;
   a proximal pressure sensor associated with the catheter; and
   a processor that receives data from the distal sensor and the proximal sensor,
   wherein the infusate pump is configured to pump infusate through the catheter to the targeted location at various flow rates, and
   wherein the processor is configured to calculate flow resistance through the targeted location by dividing a change in pressure drop between the distal and proximal sensors by a corresponding change in the infusate flow rate created by the infusate pump.

14. The system of claim 13 further comprising a balloon attached to the catheter.

15. The system of claim 13 wherein the distal sensor is attached to a guidewire.

16. The system of claim 13 wherein the distal sensor is attached to the catheter.

17. The system of claim 14 wherein the distal sensor is attached to the balloon.

18. The system of claim 13 wherein the proximal sensor is attached to the catheter.

19. The system of claim 14 wherein the proximal sensor is attached to the balloon.

20. The system of claim 14 wherein the balloon is an occluding balloon.

* * * * *